United States Patent [19]

Haun et al.

[11] Patent Number: 4,634,799
[45] Date of Patent: Jan. 6, 1987

[54] PRODUCT RECOVERY METHOD FOR DEHYDROCYCLODIMERIZATION PROCESS

[75] Inventors: Edward C. Haun, Glendale Heights; David A. Hamm, Hinsdale, both of Ill.

[73] Assignee: UOP Inc., Des Plaines, Ill.

[21] Appl. No.: 800,245

[22] Filed: Nov. 21, 1985

[51] Int. Cl.⁴ .............................................. C07C 15/42
[52] U.S. Cl. .................................................. 585/415
[58] Field of Search ........................................ 585/415

[56] References Cited

U.S. PATENT DOCUMENTS

| | | | |
|---|---|---|---|
| 2,992,283 | 7/1961 | Sarnia | 260/673 |
| 3,101,261 | 8/1963 | Skarstrom | 55/58 |
| 3,431,195 | 3/1969 | Storch et al. | 208/101 |
| 3,537,978 | 11/1970 | Borst, Jr. | 208/101 |
| 3,574,089 | 4/1971 | Forbes | 208/101 |
| 3,843,740 | 10/1974 | Mitchell et al. | 260/673 |
| 4,180,689 | 12/1979 | Davies et al. | 585/407 |
| 4,329,532 | 5/1982 | Conn et al. | 585/407 |
| 4,347,394 | 8/1982 | Detz et al. | 585/419 |
| 4,444,988 | 4/1984 | Capsuto et al. | 585/415 |
| 4,528,412 | 7/1985 | Steacy | 585/415 |

Primary Examiner—Curtis R. Davis
Attorney, Agent, or Firm—Thomas K. McBride; John F. Spears, Jr.

[57] ABSTRACT

A process flow for hydrogen-producing processes such as reforming or dehydrocyclodimerization is disclosed. A portion of a $C_3$ or $C_4$ feed stream is flashed to provide reflux cooling for a product recovery fractionation column. The cool overhead of this column and a second portion of the feed stream are used to cool the still uncondensed portion of the partially condensed reaction zone effluent stream prior to passage of this uncondensed material into a final low temperature separation stage. A second feature is the reboiling of a fractionation column with hot compressed gas to perform interstage cooling in the product recovery compression section.

25 Claims, 1 Drawing Figure

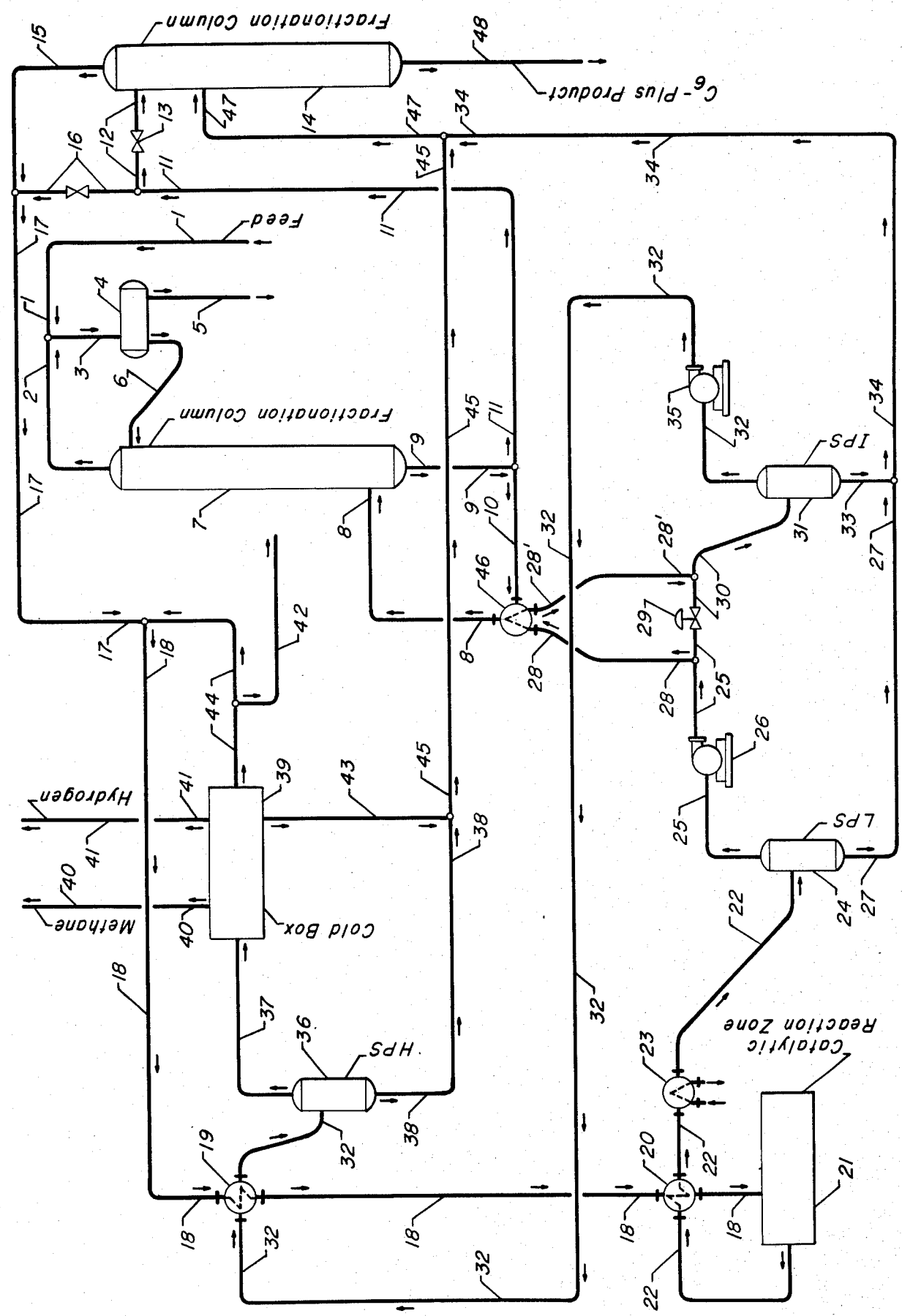

PRODUCT RECOVERY METHOD FOR DEHYDROCYCLODIMERIZATION PROCESS

FIELD OF THE INVENTION

The subject process relates to a hydrocarbon conversion process. Specifically, the subject process relates to a catalytic process referred to as dehydrocyclodimerization wherein two or more molecules of a light aliphatic hydrocarbon, such as propane or butane, are joined together to form a product aromatic hydrocarbon. Nonaromatic $C_6$-plus hydrocarbons are also produced, especially when substantial amounts of olefins are present in the feed. The invention specifically relates to the separatory methods used to recover hydrogen and product $C_6$-plus hydrocarbons from a vapor phase dehydrocyclodimerization reaction zone effluent stream. This separatory method also relates to techniques for recycling unconverted feed hydrocarbons to the reaction zone.

INFORMATION DISCLOSURE

There are a large number of references which describe the conversion of light aliphatic hydrocarbons to aromatic hydrocarbons. For instance, U.S. Pat. No. 2,992,283 issued to J. Eng describes the conversion of propylene to a variety of higher molecular weight hydrocarbons using a treated crystalline aluminosilicate as the catalyst. U.S. Pat. No. 4,347,394 issued to C. M. Detz et al describes the conversion of $C_5$-plus hydrocarbons to aromatics using a nonacidic zeolite supporting a platinum compound. U.S. Pat. No. 4,329,532 issued to P. J. Conn et al describes the conversion of $C_4$-minus olefins or mixtures of olefins and paraffins to aromatic hydrocarbons. The catalyst comprises a crystalline silicate having a specified composition, crystallite size range, and X-ray diffraction pattern. U.S. Pat. No. 4,444,988 issued to L. M. Capsuto et al describes a process flow for the recovery of the products of a similar process consuming a $C_2$–$C_5$ olefinic feedstock. The emphasis of this patent is the use of heat exchange to improve the economics of condensing hydrocarbons from the reaction zone effluent stream.

U.S. Pat. No. 4,180,689 issued to E. E. Davies et al describes the conversion of $C_3$–$C_8$ aliphatic hydrocarbons to aromatic hydrocarbons in a process which employs a catalyst comprising gallium supported on an aluminosilicate. U.S. Pat. No. 3,761,389 issued to L. D. Rollman et al describes an improved process for converting $C_2$ to 400 degrees Fahrenheit hydrocarbons to aromatics over a ZSM-5 type catalyst. The improvement resides in the use of two reaction stages in series, with the first being at more severe operating conditions. U.S. Pat. No. 3,843,740 issued to T. O. Mitchell et al also describes a process for aromatizing aliphatic feedstocks using two different catalysts in the reactor. This reference is also pertinent for the process diagram illustrating the recovery of the product aromatics by fractionation.

The separation of product hydrocarbons from a reaction zone effluent stream which also contains light hydrocarbons and possibly hydrogen is important to the successful operation of several hydrocarbon conversion processes. For instance, U.S. Pat. Nos. 3,537,978 issued to W. B. Borst, Jr. and 3,574,089 issued to J. T. Forbes describe the recovery of naphtha, hydrogen-rich recycle gas, and light hydrocarbon streams from the effluent of a catalytic reforming zone. U.S. Pat. No. 3,101,261 issued to C. W. Skarstrom illustrates a process to recover hydrogen, light ends and naphtha from the effluent of a reforming reaction zone. These references are pertinent for their showing of the use of such separatory techniques as partial condensation and stripping columns. U.S. Pat. No. 3,431,195 is pertinent for showing a reactor effluent flow in which the gaseous portion of a partially condensed reactor effluent is compressed.

It is common knowledge that it is very desirable to cool the effluent gas of a first compressor before passing this gas into a second stage of compression. Multiple stages of compression are normally more economical and may be the only commercially feasible method of significantly pressurizing large volumes of gas. It is also well known in the art that when the gas being compressed contains condensable hydrocarbons it is advisable to employ a vapor-liquid separator downstream of the interstage cooler to prevent condensate formed in the cooler from entering the next compression stage.

U.S. Pat. No. 4,528,412 issued to P. C. Steacy is pertinent for its description of a product recovery method for dehydrocyclodimerization processes. In this process flow a $C_3$ or $C_4$ feed stream of line 1 is passed into the upper portion of a debutanizer column 2. The overhead vapor of this column is charged to the reactor.

BRIEF SUMMARY OF THE INVENTION

The invention is a unique process flow which reduces the costs of dehydrocyclodimerization and other hydrogen producing processes. The invention is characterized by the method in which the feed stream is used as a coolant to reduce the utilities costs of product recovery fractionation and to aid in the separation of the reactor effluent. Another characteristic feature of the invention resides in using heat produced by interstage compression of the reactor effluent vapors to reboil a fractionation column. A broad embodiment of the invention may be characterized as a process which comprises the steps of passing at least a portion of a feed stream, which comprises $C_3$ and/or $C_4$ feed hydrocarbons, into an upper portion of a first fractional distillation zone operated under conditions such that the entering feed stream hydrocarbons function as reflux liquid to the first distillation zone and that hydrocarbons charged to the first distillation zone are separated therein into a net overhead vapor stream comprising $C_3$ and/or $C_4$ hydrocarbons and a net bottoms stream comprising $C_6$-plus hydrocarbons which is withdrawn from the process as a product; heating the overhead vapor stream and a hereinafter characterized recycle stream by indirect heat exchange against a hereinafter characterized first process stream, and then passing the overhead vapor stream and the recycle stream into a catalytic reaction zone maintained at conversion conditions and wherein $C_6$-plus hydrocarbons and hydrogen are produced, and producing a reaction zone effluent stream comprising methane, ethane, $C_3$ and/or $C_4$ hydrocarbons, hydrogen and $C_6$-plus hydrocarbons; separating the reaction zone effluent stream by a series of steps comprising cooling, partial condensation and vapor-liquid separation into a vapor-phase second process stream comprising hydrogen, ethane and $C_3$ and/or $C_4$ hydrocarbons and a liquid-phase third process stream which comprises $C_6$-plus hydrocarbons and $C_3$ and/or $C_4$ hydrocarbons; passing the third process stream into the first fractional distillation zone; passing at least a portion of the second process stream through an indirect heat exchange means as said first process stream, partially condensing the first process stream, and producing a vapor-phase fourth process stream, comprising hydrogen and ethane, methane, and a liquid phase fifth process stream, which comprises $C_3$ and/or $C_4$ hydrocarbons; separating the vapor-phase fourth process streams by a series of steps comprising partial condensation and vapor-liquid separation into a vapor-phase sixth process stream, comprising ethane, a hydrogen-rich seventh process stream which comprises methane and a liquid-phase eighth process stream comprising $C_3$ and/or $C_4$ hydrocarbons; passing at least a portion of the fifth and eighth process streams into the first fractional distillation zone; and recycling at least a portion of the sixth process stream as the previously referred to recycle stream.

BRIEF DESCRIPTION OF THE DRAWING

The drawing is a simplified diagram of a process which converts a propane-containing mixture fed to a drying column 7 through line 1 into $C_6$-plus aromatics removed in line 48. The drying column is reboiled by heat from the interstage compression of reactor effluent vapors of lines 28. At least a portion of dried feed is flashed into product column 14 via line 12 to provide reflux, with the cool overhead vapor and other portion of the feed, which is also flashed, being used to cool reactor effluent vapor in heat exchanger 19.

DETAILED DESCRIPTION

The subject invention can be applied to a wide variety of hydrogen producing hydrocarbon conversion processes. For instance, the subject invention may be employed in a hydrodealkylation process or in the catalytic reforming of naphthas as is performed to increase the octane number or aromatics content of the naphtha boiling range hydrocarbon fraction charged to this process. The identity of the actual process to which the subject invention is employed will greatly affect the preferred catalyst, feedstocks, operating conditions and other topics relevant to a discussion of the use of the invention. The process being performed will also determine the composition of the various process streams. For instance, in a reforming process there will be only small quantities of propane, ethane, and other light hydrocarbons formed as by-products. The composition of the reactor effluent will therefore comprise basically $C_6+$ hydrocarbons and hydrogen and there will be only small amounts of propane present in the gas and liquid streams being processed. On the other hand, if the subject invention is applied to a process such as dehydrocyclodimerization in which the feedstock may comprise propane or butane and $C_6+$ hydrocarbons are the products then it is expected that many of the process streams involved in the process will contain sizable amounts of propane, perhaps to the near exclusion of $C_6+$ hydrocarbons and/or hydrogen. The preferred embodiment of the subject invention is found in its application to a dehydrocyclodimerization process. Therefore, the remainder of this description of the invention will be skewed towards a process for dehydrocyclodimerization.

Processes for the conversion of light aliphatic hydrocarbons to aromatic or nonaromatic $C_6$-plus hydrocarbons have been the subject of significant development efforts as evidenced by the previously cited references. The basic utility of the process is the conversion of the low cost highly available $C_3$ and/or $C_4$ hydrocarbons into the more valuable aromatic hydrocarbons and hydrogen or to convert the feed hydrocarbons to higher molecular weight aliphatic products. This may be desired simply to upgrade the value of the hydrocarbons. It may also be desired to correct an overabundance of the $C_3$ and $C_4$ hydrocarbons or to fulfill a need for the aromatic hydrocarbons. The aromatic hydrocarbons are highly useful in the production of a wide range of petrochemicals, with benzene being one of the most widely used basic feed hydrocarbon chemicals. The product aromatic hydrocarbons are also useful as blending components in high octane number motor fuels.

The feed compounds to a dehydrocyclodimerization process are light aliphatic hydrocarbons having from 2 to 4 carbon atoms per molecule. The feed stream may comprise a single compound or a mixture of two or more of these compounds. The preferred feed compounds are propane, propylene, the butanes, and the butylenes, with saturates being highly preferred. The feed stream to the process may also contain some $C_2$ and $C_5$ hydrocarbons. It is preferred that the concentration of $C_5$ hydrocarbons in the feed stream to a dehydrocyclodimerization process is held to the minimum practical level. The preferred products of the process are $C_6$-plus aromatic hdyrocarbons. However, dehydrocyclodimerization processes are not 100% selective and some nonaromatic $C_6$-plus hydrocarbons are produced even from saturate feeds. When processing a feed made up of propane and/or butanes, the very great majority of the $C_6$-plus product hydrocarbons will be benzene, toluene, and the various xylene isomers. A small amount of $C_9$-plus aromatics is also produced. The presence of olefins in the feed stream results in increased production of $C_6$-plus long chain hydrocarbons as products with the preferred catalyst system. Sizable olefin concentrations in the feed significantly decrease the production of aromatics.

The subject invention is directed to the recovery of the product hydrocarbons from the effluent stream of a reaction zone. Therefore, the configuration of the reaction zone and the composition of the catalyst employed within the reaction zone are not basic elements of the invention or limiting characteristics of the invention. Nevertheless, in order to provide a background to the subject invention, it is felt useful to describe the preferred reactor system for use in the reforming and dehydrocyclodimerization embodiments of the invention. This system comprises a moving bed radial flow multistage reactor such as is described in U.S. Pat. Nos. 3,652,231; 3,692,496; 3,706,536; 3,785,963; 3,825,116; 3,839,196; 3,839,197; 3,854,887; 3,856,662; 3,918,930; 3,981,824; 4,094,814; 4,110,081; and 4,403,909. These patents also describe catalyst regeneration systems and various aspects of moving catalyst bed operations and equipment. This reactor system has been widely employed commercially for the reforming of naphtha fractions. Its use has also been described for the dehydrogenation of light paraffins.

The preferred moving bed reactor system employs a spherical catalyst having a diameter between about 1/64 and ⅛ inch. The catalyst preferably comprises a support material and a metallic component deposited on the support material as through impregnation or coprecipitation. The previously cited references point out that the current trend is the use of a zeolitic support material, with the catalyst referred to in the art as a ZSM-5 type zeolite being often specified as a preferred material. European patent application No. 832011422.9 by E. P. Kieffer may be consulted for information on zeolite-containing dehydrocyclodimerization catalysts. When properly formulated, it appears this zeolitic material by itself has significant activity for the dehydrocyclodimerization reaction. However, it is still preferred to employ a metallic component within the catalyst system to increase the activity of the catalyst. The preferred metallic component is gallium as described in the previously cited U.S. Pat. No. 4,180,689. A dehydrocyclodimerization reaction zone is preferably operated at a temperature between about 920 degrees–1100 degrees Fahrenheit (487 degrees–593 degrees Centigrade) and a pressure under 100 psig (689 kPag). Hydrogen-producing reactions are normally favored by lower pressures, and pressures under about 70 psig (483 kPag) at the outlet of the reaction zone are highly preferred. Other conditions may be preferred for other reactions.

The drawing illustrates the preferred embodiment of the invention. Those skilled in the art will recognize that this process flow diagram has been simplified by the elimination of many pieces of process equipment including some heat exchangers, process control systems, pumps, fractionation column overhead and reboiler systems, etc. which are not necessary to an understanding of the process. It may also be readily discerned that the process flow presented in the drawing may be modified in many aspects without departing from the basic overall concept of the invention. For example, the heat exchangers shown in the drawing have been held to a minimum for purposes of simplicity. Those skilled in the art will recognize that the choice of heat exchange methods employed to obtain the necessary heating and cooling at various points within the process is subject to a large amount of variation as to how it is performed. In a process as complex as this, there exists many possibilities for indirect heat exchange between different process streams. Depending on the specific location and circumstance of the installation of the subject process, it may also be desired to employ heat exchange against steam, hot oil, or process streams from other processing units not shown on the drawing.

Referring now to the drawing, a stream of relatively high purity propane enters the process through line 1 and is admixed with the overhead vapor of the drying column 7 which is carried by line 2. This admixture flows through line 3 into the overhead receiver 4. The cooling provided by the feed stream and by a cooling means results in the condensation of essentially all of the propane entering the overhead receiver. The liquefied propane is returned to the drying column through line 6. Water present in the feed stream and overhead vapor stream is also condensed and is separated from the less dense liquid propane by decantation and withdrawn through line 5. The thus dried feed propane emerges as a liquid from the bottom of the drying column 7 through line 9. A first portion of the propane passes through line 10 and the reboiler 46 wherein it is at least partially vaporized. The resultant vapors are passed into a lower portion of the drying column 7 through line 8.

The remaining net bottoms stream is the feed to the process and flows through line 11 before being divided into a first portion carried by line 12 and a second portion carried by line 16. The portion of the feed propane flowing through line 12 is flashed to a lower pressure as it passes through flow control valve 13. This procedure generates relatively low temperature vapor and liquid which is passed into the upper portion of the product fractionation column 14. The cool liquid performs the necessary refluxing function at the top of this fractional distillation column. The cool vapor leaves through the top of column. The overhead vapor stream removed from column 14 in line 15 will basically comprise propane but will also contain any butane, hydrogen, ethane or methane which is dissolved in the liquid phase hydrocarbon streams charged to the column through line 47.

The relatively cool overhead vapor stream of line 15 is admixed with the second portion of the feed stream which is also flashed through a valve to produce relatively low temperature vapor and liquid, if the entire feed stream does not flow through line 12, and is then passed into line 17. The hydrocarbons flowing through line 17 are admixed with an ethane rich stream from line 44 and are then passed through line 18. The material flowing through line 18 is quite cool and is employed as a coolant in the indirect heat exchange means 19. In this heat exchange means, the material flowing through line 18 is heated to a temperature closer to the desired inlet temperature of the downstream catalytic reaction zone 21. Simultaneously, the material flowing through line 32 is cooled thereby aiding the partial condensation of this material and its separation into vapor and liquid portions in the high pressure separator 36. The hydrocarbons flowing through line 18 are further heated in the feed-effluent heat exchange means 20 and possibly by other heat exchange means not shown. The resultant heated material, together with any recycle hydrogen if so desired, is then passed through a catalytic reaction zone such as the preferred dehydrocyclodimerization zone wherein the propane and other light hydrocarbons are at least partially converted to $C_6+$ product hydrocarbons. In the dehydrocyclodimerization and reforming processes, this will also result in the simultaneous production of hydrogen.

The effluent stream of the catalytic reaction zone 21 will therefore preferably comprise an admixture of residual components of the feed stream such as propane and/or butane, hydrogen, $C_6+$ aromatics such as benzene, toluene, and xylene, by-product or recycled ethane and by-product methane. The reaction zone effluent stream is first cooled in the heat exchanger 20 and then in the supplemental indirect heat exchange means 23. This results in a partial condensation of the materials flowing through line 22 such that they may be separated into a vapor phase and a liquid phase in the low pressure separator 24. The liquid phase removed from separator 24 is transferred as a process stream through lines 27 and 34 to the product fractionation column 14.

The vapor phase material collected in the low pressure separation zone is removed through line 25 and pressurized in the compressor 26. The pressurization of this vapor phase material increases its temperature. A portion or all of the material flowing through line 25 may therefore be diverted through the operation of valve 29 through line 28 to serve as the heating media for reboiler means 46. The thus cooled vapor phase material or partially condensed material returns through line 28' and flows into line 30. Additional indirect heat exchangers may be located in line 30 to effect further cooling of the materials flowing therethrough. The resultant partially condensed mixture then flows into an intermediate pressure separation zone 31. The liquid phase material such as condensed propane and/or butane and $C_6+$ hydrocarbons are removed from the intermediate pressure separator as another process stream carried by line 33. It is also charged to the fractionation column 14 via lines 34 and 47. The liquid phase streams removed from the low pressure separation zone and the intermediate pressure separation zones will have dissolved in them an equilibrium amount of more volatile hydrocarbons such as ethane and methane and hydrogen.

The vapor phase material separated in the intermediate pressure separator is withdrawn as a vapor phase process stream through line 32 and pressurized in the compressor 35. The thus pressurized material flows through line 32 to the indirect heat exchange means 19 wherein it is cooled. An additional indirect heat exchange means not shown would normally be employed in this line to effect further cooling and a partial condensation of the material flowing through line 32 upstream of exchanger 19. The material flowing through line 32 is thereby partially condensed prior to the passage into the high pressure separator 36. The separation of the incoming fluids results in the production of the additional liquid phase process stream comprising condensed propane and/or butane and dissolved light hydrocarbons carried by line 38 and a vapor phase stream having a relatively low concentration of $C_6+$ hydrocarbons but containing substantial amounts of hydrogen and lighter hydrocarbons.

The vapor phase process stream of line 37 is passed into a "cold box" 39 wherein by cryogenic separation high purity streams of the various components of the process stream of line 37 are produced. This results in the production of a highly concentrated methane stream removed in line 40, a hydrogen rich vapor stream removed from the process in line 41, a vapor phase stream comprising predominantly ethane withdrawn in line 44 and a liquid phase stream of mainly propane and/or butane withdrawn through line 43. A controlled portion of the ethane can be withdrawn through line 42. The liquid phase stream of line 43 is combined with the process stream of line 38 and passed through lines 45 and 47 into the product fractionation column 14. The product fractionation column 14 is operated in a manner to separate the entering hydrocarbon streams into a $C_6+$ net bottoms stream withdrawn from the process in line 48 and the overhead vapor stream of line 15.

The subject invention reduces the utilities costs of operating the process to which it is applied. It may also reduce the capital cost of the required plant. The subject invention eliminates the requirement for providing and operating an overhead condenser for the product fractionation column. The reduced temperature of the feed stream allows the remaining vapors being charged to the high pressure separator to be cooled to a greater extent by indirect heat exchange. More condensation of this stream can thereby be performed using the same amount of external cooling. This can be used to reduce the gas flow to and required capacity of the cold box. Alternatively, the amount of external cooling can be reduced while keeping condensation and overall cooling constant. Finally, the use of interstage compression heat to reboil a fractionator reduces or eliminates the fuel costs previously required to perform this necessary heating.

As previously mentioned, the invention may be applied to the production and recovery of hydrogen and $C_6+$ hydrocarbons from a variety of processes including those which produce mainly aromatic products such as reforming and dehydrocyclodimerization. Some such processes are described in the previously cited references. In some instances, the composition of the reactor effluent is very dependent upon the feed composition. For instance, the processing of a highly olefinic feed stream with preferred reaction conditions and gallium containing catalyst system will result in a product slate of over 50 mole percent aliphatics instead of the aromatics usually associated with dehydrocyclodimerization. The recovered $C_6+$ hydrocarbons may therefore include hexanes, heptanes, octanes, nonanes and other paraffinic compounds containing from six to twelve carbon atoms per molecule. The same process flow may still be employed.

The preferred embodiment of the invention is a dehydrocyclodimerization process which comprises the steps of passing at least a portion of a feed stream, which comprises $C_3$ and/or $C_4$ feed hydrocarbons, into an upper portion of a first fractionation column operated under conditions such that the entering feed stream hydrocarbons function as reflux liquid to the fractionation column and that hydrocarbons charged to the first fractionation column are separated therein into a net overhead vapor stream comprising $C_3$ and/or $C_4$ hydrocarbons and a net bottoms stream comprising $C_6$-plus hydrocarbons which is withdrawn from the process as a product; heating the overhead vapor stream and a hereinafter characterized recycle stream in a heat exchange means by indirect heat exchange against a hereinafter characterized first process stream, and then passing the overhead vapor stream and the recycle stream into a catalytic reaction zone maintained at conversion conditions and wherein $C_6$-plus hydrocarbons and hydrogen are produced, and producing a reaction zone effluent stream comprising methane, ethane, $C_3$ and/or $C_4$ hydrocarbons, hydrogen and $C_6$-plus aromatic hydrocarbons; separating the reaction zone effluent stream by a series of steps comprising cooling, partial condensation and vapor-liquid separation into a vapor phase second process stream comprising $C_6$-plus aromatic hydrocarbons, hydrogen, methane, ethane and $C_3$ and/or $C_4$ hydrocarbons and a liquid-phase third process stream which comprises $C_6$-plus aromatic hydrocarbons and $C_3$ and/or $C_4$ hydrocarbons; compressing, cooling and partially condensing the second process stream and forming a vaporphase fourth process stream, which comprises hydrogen, methane, ethane, $C_3$ and/or $C_4$ hydrocarbons and $C_6$-plus aromatic hydrocarbons, and a liquid-phase fifth process stream comprising $C_3$ and/or $C_4$ hydrocarbons and $C_6$-plus aromatic hydrocarbons; passing the third and the fifth process streams into the first fractionation column; passing at least a portion of the fourth process stream through an indirect heat exchange means as said first process stream, partially condensing the first process stream, and producing a vapor-phase sixth process stream, comprising $C_3$ and/or $C_4$ hydrocarbons, hydrogen, methane, and ethane, and a liquid phase seventh process stream, which comprises $C_3$ and/or $C_4$ hydrocarbons and $C_6$-plus hydrocarbons; separating the vapor-phase sixth process streams by a series of steps comprising partial condensation and vapor-liquid separation into a vapor-phase eighth process stream, comprising ethane, a hydrogen-rich ninth process stream and a liquid-phase tenth process stream comprising $C_3$ and/or $C_4$ hydrocarbons; passing at least a portion of the seventh and tenth process streams into the first fractionation column; and recycling at least a portion of the eighth process stream to the reaction zone as the previously referred to recycle stream. Hydrogen may be added to the ethane-rich stream to recycle hydrogen to the reaction zone or a portion of the hydrogen-rich stream itself may be recycled.

It is believed that those skilled in the art of petroleum and petrochemical process design may determine proper operating conditions, vessel designs, and operating procedures for the subject process through the use of standard process design techniques after having now been appraised of the overall flow of the process. These design techniques should include a recognition that it is undesirable to pass compounds which may tend to freeze or otherwise solidify into the low temperature portion of the process. For this reason, a drying zone may be provided. The function of this drying zone would be to prevent the passage of water into the low temperature equipment. The drying zone is basically required to remove the small amount of water which may be dissolved within a feed stream to the process and/or any water which may be present on regenerated catalyst passed into the process. The drying zone is preferably a swing bed desiccant-type system. It is preferred to use two beds of a suitable absorbent alumina, with facilities being provided to regenerate one of these beds while the other bed is on-stream.

The vapor-liquid separation zones employed within the process preferably comprise a suitably sized vertically oriented vessel having a demisting pad or other liquid entrainment removal means provided at the upper end. The fractionation zones employed in the process preferably contain a single trayed fractionation column having sieve-type trays and being of relatively standard design. For instance, a properly designed column having 30 trays will function as the drying column, and the product recovery column may also contain 30 trays. Multicolumn fractionation zones may of course be employed if so desired. Suitable fractionation zones may be readily designed by those skilled in the art. The operating conditions required in the fractionation zones is dependent upon the compounds being separated and the desired separation.

The following example is presented to more fully characterize and describe the subject invention. The example is based on the preferred process flow as shown in the drawing. The example is based upon detailed engineering studies of a proposed commercial unit using the best data available to predict the operation of the unit. The charge stream is a 10,000 barrel per day (BPD) stream of pure propane, which is equivalent to 1680 moles per hour. This stream is passed into the overhead receiver of the 30 tray drying column. The combined reflux liquid and charge is passed into the top of the column at a temperature of 38 degrees Centigrade (100 degrees Fahrenheit), with the column being operated at a top pressure of 1248 kPag (181 psig) and a reflux ratio of 2.0. The column is reboiled by heat provided by the compression of uncondensed reactor effluent vapors in the first stage of compression. The drying column is operated at a bottoms temperature of 40 degrees Centigrade (104 degrees Fahrenheit) at a pressure of 1282 kPag (186 psig). The net bottoms stream has a flow rate of 1680 moles per hour and becomes the feed stream to the rest of the process.

A portion of the drying column net bottoms stream having a flow rate of about 640 moles per hour is flashed to provide cool liquid and vapor charged to the top of a depropanizer column to provide the necessary cooling at the top of the column. The depropanizer overhead vapor stream has a flow rate of approximately 1262 moles per hour, a temperature of 18 degrees Centigrade (65 degrees Fahrenheit) and a pressure of 690 kPag (100 psig). The depropanizer overhead vapor contains about 1.0 moles per hour of hydrogen, with the rest being hydrocarbons. The depropanizer overhead vapor stream is combined with the other portion of the feed stream and with an ethane rich stream from the cold box having a flow rate of about 1456 moles per hour, of which about 20 moles per hour is hydrogen. The admixture of these three streams forms a mixed-phase stream having a temperature of about $-9$ degrees Centigrade (15 degrees Fahrenheit). This combined stream is used to cool the compressed gas emanating from the third stage of compression. It is then passed through a feed-effluent heat exchanger wherein it is heated to 463 degrees Centigrade (866 degrees Fahrenheit). The combined feed stream is then heated to about 579 degrees Centigrade (1075 degrees Fahrenheit) and passed into the first stage of a four reaction stage reaction zone having interstage heaters between each reaction stage. The interstage heaters are required due to the endothermic nature of the dehydrocyclodimerization reaction. The reactants are contacted with dehydrocyclodimerization catalyst in each reaction stage to effect the production of $C_6+$ aromatic hydrocarbons and hydrogen.

The reaction zone effluent stream emerges from the last reaction stage at a pressure of about 83 kPag (12 psig). It has a flow rate of approximately 5,938 moles per hour and is cooled to about 56 degrees Centigrade (132 degrees Fahrenheit) in the combined feed-effluent heat exchanger. This stream is then further cooled to about 38 degrees Centigrade (100 degrees Fahrenheit) by another heat exchange device and passed into the low pressure separator. The cooling of this stream causes the condensation of a sizeable amount of $C_6+$ hydrocarbons allowing the removal of a liquid stream having a flow rate of about 199 moles per hour. The remaining vapors are withdrawn at a pressure of 27.6 kPag (4 psig) and passed into the first compression stage. This vapor stream is compressed to approximately 758 kPag (110 psig) and, after allowing spillback, there is produced a vapor stream having a flow rate of about 5738 moles per hour and a temperature of about 180 degrees Centigrade (356 degrees Fahrenheit). A portion of this compressed gas stream is used to reboil the drying column. After being cooled in this manner the compressed gas is combined with second stage spillback gas, to produce a gas having a temperature of about 108 degrees Centigrade (227 degrees Fahrenheit) and a pressure of near 724 kPag (105 psig). The gas is cooled to 38 degrees Centigrade (100 degrees Fahrenheit) in coolers and is then passed into an intermediate stage separation zone. An additional 233 moles per hour of liquid hydrocarbons are withdrawn for passage to the depropanizer column. The net vapor from this vapor-liquid separation is compressed to about 3827 kPag (555 psig). The compressed vapor is then cooled by indirect heat exchange against the combined feed stream and an additional cooler not shown in the drawing. This causes the partial condensation of the vapor to produce the mixed-phase stream which enters the high pressure separator at a temperature of about 5 degrees Centigrade (40 degrees Fahrenheit). A vapor stream having a flow rate of approximately 5,404 moles per hour is withdrawn from the high pressure separator and passed into the cold box. A liquid stream of about 101 moles per hour is also withdrawn from the high pressure separator and is passed into the depropanizer column. The material fed to the cold box is separated into a hydrogen product stream having a flow rate of about 2100 moles per hour, a methane product stream of approximately 841 moles per hour, an ethane stream of about 1855 moles per hour and a propane rich stream of about 608 moles per hour. The propane rich stream is passed into the depropanizer, and the ethane is split between the ethane recycle stream and a net product stream.

The total feed to the depropanizer column is about 1141 moles per hour. The various streams fed to the column, excluding of course the propane used as reflux, are heated to 99 degrees Centigrade (210 degrees Fahrenheit) prior to being passed into the column. The net bottoms stream of the column has an average molecular weight of 92.1, a flow rate of about 511 moles per hour and a temperature near 193 degrees Centigrade (379 degrees Fahrenheit). This net bottoms stream will contain the $C_4$-plus hydrocarbons produced in the process such as pentane in addition to $C_6$-plus aromatics and a small amount of $C_6$-plus acyclic compounds. The major components of the net bottoms stream will be benzene, toluene, and xylenes.

The term "cold box" is used extensively in the process design arts to indicate a collection of equipment for recovering less volatile (more condensable) compounds from a mixture containing a sizeable amount of a highly volatile gas such as methane or hydrogen. Cold boxes are available commercially from a number of suppliers, and the design and equipment would normally vary between the competing suppliers. A typical cold box will expose the entering compounds to a relatively low temperature to effect an added condensation of the entering less volatile compounds and thereby produce a first stream comprised mainly of hydrogen and a second stream comprised mainly of ethane and propane and heavier hydrocarbons. The cold temperature required for this may be provided through absorptive refrigeration or by the expansion or flashing of fluids circulating or employed within the cold box itself. The cold box would therefore normally contain at least one indirect heat exchanger, and one or more vapor-liquid separation vessels. The separation of hydrogen and methane will basically be performed by exposing a gas containing principally hydrogen and methane to a temperature sufficiently low to condense the methane. As stated above, the ethane and propane entering the cold box will also be concentrated into a stream comprised principally of these two compounds. They may then be separated by fractional distillation in a deethanizer column.

The compression train shown in the drawing is the preferred configuration. However, it will be recognized that the benefits provided by cooling the effluent of a compressor handling a process stream in this manner will also be desirable if the compression train only comprises a single compressor or if it comprises three or more compressors in series. Therefore, the heat present in the newly compressed uncondensed portion of the reaction zone effluent stream may be extracted for use in reboiling a fractionation zone at the point shown in the drawing or at an alternative point such as downstream of the compressor 35. Another alternative equipment arrangement would comprise the utilization of the heat of compression of the effluents of two different compressors. This heat could be employed to reboil the same fractionation column, to reboil different fractionation columns or to supply heat at different elevations within a single fractionation column.

The fractionation column(s) reboiled through the use of the high temperature gas stream produced during compression is preferably a feed drying column as shown in the drawing. The heat available in this gas stream may be employed in reboiling fractionation columns operated for other purposes. For instance, the fractionation column could be located in a different process unit and would perhaps dry or in other ways prepare a feed stream for introduction into this other process unit. Depending upon the temperature of the compressed gas and the operating pressure of the fractionation column, the heat available in the compressed gas could possibly also be employed in a column drying other hydrocarbons or performing a separation of two or more hydrocarbons such as the separation of ethane or propane from a heavier hydrocarbon such as butane. The heat available in the compressed gas could also be employed for stripping other impurities such as oxygen or oxygenated hydrocarbons from a hydrocarbon mixture as part of a feed preparation step. It may also be possible to employ the heat present in the compressed gas to aid in the operation of the product fractionation column.

This embodiment, which uses the interstage heat in reboiling a fractionation column, may be characterized as a hydrogen producing process which comprises the steps of: passing a feed stream into a catalytic reaction zone maintained at conversion conditions and wherein $C_6$-plus hydrocarbons and hydrogen are produced, and producing a reaction zone effluent stream comprising ethane, hydrogen and $C_6$-plus hydrocarbons; separating the reaction zone effluent stream by a series of steps comprising cooling, partial condensation and vapor-liquid separation into a vapor-phase first process stream comprising hydrogen and ethane and a liquid-phase second process stream which comprises $C_6$-plus hydrocarbons; passing the second process stream into a first fractional distillation zone and recovering $C_6$-plus hydrocarbons from the first fractional distillation zone; heating the vapor-phase first process stream by compression; cooling the first process stream by indirect heat exchange, with the first process stream being employed as a heating media used to reboil a second fractional distillation zone, and partially condensing the first process stream; and, separating the thus partially condensed first process stream into a liquid-phase third process stream and a vapor-phase fourth process stream having a higher concentration of hydrogen than the first process stream.

We claim as our invention:

1. A hydrogen producing hydrocarbon conversion process which comprises the steps of:
   (a) passing a feed stream comprising a $C_2$–$C_5$ hydrocarbon into a catalytic reaction zone maintained at conversion conditions including a temperature of about 920–1100 degrees Fahrenheit and a pressure under 100 psig and wherein $C_6$-plus hydrocarbons and hydrogen are produced, and producing a reaction zone effluent stream comprising ethane, hydrogen and $C_6$-plus hydrocarbons;
   (b) separating the reaction zone effluent stream by a series of steps comprising cooling, partial condensation and vapor-liquid separation into a vapor-phase first process stream comprising hydrogen and ethane and a liquid-phase second process stream which comprises $C_6$-plus hydrocarbons;
   (c) passing the second process stream into a first fractional distillation zone and recovering $C_6$-plus hydrocarbons from the first fractional distillation zone;

(d) heating the vapor-phase first process stream by compression;

(e) cooling the first process stream by indirect heat exchange, with the first process stream being employed as a heating media used to reboil a second fractional distillation zone, and partially condensing the first process stream; and, (f) separating the thus partially condensed first process stream into a liquid-phase third process stream and a vapor-phase fourth process stream having a higher concentration of hydrogen than the first process stream.

2. The process of claim 1 further characterized in that hydrogen present in the fourth process stream is recycled to the reaction zone.

3. The process of claim 1 further characterized in that hydrogen present in the fourth process stream is discharged from the process as a product stream.

4. The process of claim 3 further characterized in that the third process stream is passed into the first fractional distillation zone.

5. The process of claim 1 further characterized in that the feed stream, the second process stream and the third process stream comprise $C_3$ and/or $C_4$ hydrocarbons.

6. The process of claim 5 further characterized in that $C_6$ hydrocarbons and hydrogen are produced in the reaction zone by the dehydrocyclodimerization of feed hydrocarbons.

7. The process of claim 6 further characterized in that the second fractional distillation zone comprises a single fractionation column from which at least a portion of the feed stream is withdrawn.

8. The process of claim 1 further characterized in that the second fractional distillation zone is operated as a drying zone.

9. A hydrocarbon conversion process which comprises the steps of:

(a) passing at least a portion of a feed stream, which comprises $C_3$ and/or $C_4$ feed hydrocarbons, into an upper portion of a first fractionation zone operated under conditions such that the entering feed stream hydrocarbons function as reflux liquid to the first fractionation zone and that hydrocarbons charged to the first fractionation zone are separated therein into a net overhead vapor stream comprising $C_3$ and/or $C_4$ hydrocarbons and a net bottoms stream comprising $C_6$-plus hydrocarbons which is withdrawn from the process as a product;

(b) heating the overhead vapor stream and a hereinafter characterized recycle stream by indirect heat exchange against a hereinafter characterized first process stream, and then passing the overhead vapor stream and the recycle stream into a catalytic reaction zone maintained at conversion conditions and wherein $C_6$-plus hydrocarbons and hydrogen are produced, and producing a reaction zone effluent stream comprising ethane, $C_3$ and/or $C_4$ hydrocarbons, hydrogen and $C_6$-plus hydrocarbons;

(c) separating the reaction zone effluent stream by a series of steps comprising cooling, partial condensation and vapor-liquid separation into a vapor-phase second process stream comprising hydrogen, ethane and $C_3$ and/or $C_4$ hydrocarbons and a liquid-phase third process stream which comprises $C_6$-plus hydrocarbons and $C_3$ and/or $C_4$ hydrocarbons;

(d) passing the third process stream into the first fractionation zone;

(e) passing at least a portion of the second process stream through an indirect heat exchange means as said first process stream, partially condensing the first process stream, and producing a vapor-phase fourth process stream, comprising $C_3$ and/or $C_4$ hydrocarbons, hydrogen and ethane, and a liquid phase fifth process stream, which comprises $C_3$ and/or $C_4$ hydrocarbons;

(f) separating the vapor-phase fourth process streams by a series of steps comprising partial condensation and vapor-liquid separation into a vapor-phase sixth process stream, comprising ethane, a hydrogen-rich seventh process stream and a liquid-phase eighth process stream comprising $C_3$ and/or $C_4$ hydrocarbons;

(g) passing at least a portion of the fifth and eighth process streams into the first fractionation zone; and (h) recycling at least a portion of the sixth process stream as the previously referred to recycle stream.

10. The process of claim 9 further characterized in that the first fractionation zone comprises a single fractionation column.

11. The process of claim 9 further characterized in that a second portion of the feed stream is also heated by indirect heat exchange against the first process stream and then passed into the reaction zone.

12. The process of claim 11 further characterized in that the first and second portions of the feed stream are withdrawn from a second fractionation zone comprising a single fractionation column.

13. The process of claim 12 further characterized in that the second fractionation zone is reboiled at least in part by indirect heat exchange against at least a portion of the vapor-phase second process stream after the second process stream has been heated by compresssion.

14. The process of claim 9 further characterized in that $C_6$ hydrocarbons and hydrogen are produced in the reaction zone by the dehydrocyclodimerization of propane.

15. The process of claim 9 further characterized in that $C_6$ hydrocarbons and hydrogen are produced in the reaction zone by the dehydrocyclodimerization of butane.

16. The process of claim 9 further characterized in that the separation of the reaction zone effluent stream comprises partial condensation followed by two vapor-phase compression steps with intermediate cooling and a second partial condensation, and with the vapor-phase second process stream being recovered from the second partial condensation.

17. The process of claim 16 further characterized in that a methane-rich vapor-phase is produced during separation of the fourth process stream and withdrawn from the process.

18. A hydrocarbon conversion process which comprises the steps of:

(a) passing at least a portion of a feed stream, which comprises $C_3$ and/or $C_4$ feed hydrocarbons, into an upper portion of a first fractionation column operated under conditions such that the entering feed stream hydrocarbons function as reflux liquid to the first fractionation column and that hydrocarbons charged to the first fractionation column are separated therein into a net overhead vapor stream comprising $C_3$ and/or $C_4$ hydrocarbons and a net bottoms stream comprising $C_6$-plus hydrocarbons which is withdrawn from the process as a product;

(b) heating the overhead vapor stream and a hereinafter characterized recycle stream in a heat exchange means by indirect heat exchange against a hereinafter characterized first process stream, and then passing the overhead vapor stream and the recycle stream into a catalytic reaction zone maintained at conversion conditions and wherein $C_6$-plus hydrocarbons and hydrogen are produced, and producing a reaction zone effluent stream comprising methane, ethane, $C_3$ and/or $C_4$ hydrocarbons, hydrogen and $C_6$-plus aromatic hydrocarbons;

(c) separating the reaction zone effluent stream by a series of steps comprising cooling, partial condensation and vapor-liquid separation into a vapor-phase second process stream comprising $C_6$-plus aromatic hydrocarbons, hydrogen, methane, ethane and $C_3$ and/or $C_4$ hydrocarbons and a liquid-phase third process stream which comprises $C_6$-plus aromatic hydrocarbons and $C_3$ and/or $C_4$ hydrocarbons;

(d) compressing, cooling and partially condensing the second process stream and forming a vapor-phase fourth process stream, which comprises hydrogen, methane, ethane, $C_3$ and/or $C_4$ hydrocarbons and $C_6$-plus aromatic hydrocarbons, and a liquid-phase fifth process stream comprising $C_3$ and/or $C_4$ hydrocarbons and $C_6$-plus aromatic hydrocarbons;

(e) passsing the third and the fifth process streams into the first fractionation column;

(f) passing at least a portion of the fourth process stream through an indirect heat exchange means as said first process stream, partially condensing the first process stream, and producing a vapor-phase sixth process stream, comprising $C_3$ and/or $C_4$ hydrocarbons, hydrogen, methane, and ethane, and a liquid phase seventh process stream, which comprises $C_3$ and/or $C_4$ hydrocarbons and $C_6$-plus hydrocarbons;

(g) separating the vapor-phase sixth process stream by a series of steps comprising partial condensation and vapor-liquid separation into a vapor-phase eighth process stream, comprising ethane, a hydrogen-rich ninth process stream and a liquid-phase tenth process stream comprising $C_3$ and/or $C_4$ hydrocarbons;

(h) passing at least a portion of the seventh and tenth process streams into the first fractionation column; and (i) recycling at least a portion of the eighth process stream to the reaction zone as the previously referred to recycle stream.

19. The process of claim 18 further characterized in that a second portion of the feed stream is passed through said heat exchange means in admixture with the overhead vapor stream and the recycle stream and heated by indirect heat exchange against the first process stream.

20. The process of claim 19 further characterized in that the first and second portions of the feed stream are both withdrawn from a single second fractionation column.

21. The process of claim 20 further characterized in that the second fractionation column is reboiled at least in part by indirect heat exchange against the vapor-phase second process stream after the second process stream has been heated by compresssion and in that the second process stream is thereby partially condensed.

22. The process of claim 18 further characterized in that $C_6$ hydrocarbons and hydrogen are produced in the reaction zone by the dehydrocyclodimerization of propane.

23. The process of claim 18 further characterized in that $C_6$ hydrocarbons and hydrogen are produced in the reaction zone by the dehydrocyclodimerization of butane.

24. The process of claim 18 further characterized in that a methane-rich vapor-phase is produced during separation of the sixth process stream and withdrawn from the process.

25. The process of claim 18 further characterized in that a solid catalyst comprising gallium on a support material is employed within the reaction zone.

* * * * *